(12) United States Patent
Hubaux et al.

(10) Patent No.: US 10,013,575 B2
(45) Date of Patent: Jul. 3, 2018

(54) METHOD TO MANAGE RAW GENOMIC DATA IN A PRIVACY PRESERVING MANNER IN A BIOBANK

(71) Applicant: Sophia Genetics S.A., Saint Sulpice (CH)

(72) Inventors: Jean-Pierre Hubaux, St-Sulpice (CH); Erman Ayday, Renens (CH); Jean-Louis Raisaro, Lausanne (CH); Urs Hengartner, Kitchener (CA); Adam Molyneaux, Blonay (CH); Zhenyu Xu, Commugny (CH); Jurgi Camblong, Bernex (CH); Pierre Hutter, Saxon (CH)

(73) Assignee: SOPHIA GENETICS S.A., Saint Sulpice (CH)

( * ) Notice: Subject to any disclaimer, the term of this patent is extended or adjusted under 35 U.S.C. 154(b) by 242 days.

(21) Appl. No.: 14/899,999

(22) PCT Filed: Jun. 17, 2014

(86) PCT No.: PCT/EP2014/062736
§ 371 (c)(1),
(2) Date: Dec. 18, 2015

(87) PCT Pub. No.: WO2014/202615
PCT Pub. Date: Dec. 24, 2014

(65) Prior Publication Data
US 2016/0275308 A1 Sep. 22, 2016

(30) Foreign Application Priority Data
Jun. 19, 2013 (EP) ..................... 13172607

(51) Int. Cl.
G06F 21/62 (2013.01)
G06F 19/28 (2011.01)
H04L 9/06 (2006.01)

(52) U.S. Cl.
CPC .......... *G06F 21/6245* (2013.01); *G06F 19/28* (2013.01); *H04L 9/065* (2013.01); *H04L 2209/04* (2013.01)

(58) Field of Classification Search
CPC ...... G06F 21/60; G06F 21/6245; G06F 19/10; G06F 19/28; H04L 9/065; H04L 2209/04
See application file for complete search history.

(56) References Cited

U.S. PATENT DOCUMENTS

| 8,126,655 B2 * | 2/2012 | Katoh ................... G06F 19/18 702/20 |
| 2012/0236861 A1 * | 9/2012 | Ganeshalingam ...... H04L 45/00 370/392 |
| 2013/0246460 A1 * | 9/2013 | Maltbie .................. G06F 19/18 707/771 |

FOREIGN PATENT DOCUMENTS

WO 2013/049420 4/2013

OTHER PUBLICATIONS

Kantarcioglu et al., A Cryptographic Approach to Securely Share and Query Genomic Sequences, Sep. 2008, IEEE Transactions on Information Technology in Biomedicine, vol. 12, No. 5.*

(Continued)

*Primary Examiner* — Khang Do
(74) *Attorney, Agent, or Firm* — Greenblum & Bernstein, P.L.C.

(57) ABSTRACT

A method to manage raw genomic data (SAM/BAM files) in a privacy preserving manner in a biobank. By using order preserving encryption of the reads' positions, the method provides a requested range of nucleotides to a medical unit, without revealing the locations of the short reads (which (Continued)

include the requested nucleotides) to the biobank. The method prevents the leakage of extra information in the short reads to the medical unit by masking the encrypted short reads at the biobank. That is, specific parts of the genomic data for which the medical unit is not authorized or the patient prefers to keep secret are masked at the biobank, without revealing any information to the biobank.

20 Claims, 5 Drawing Sheets

(56) References Cited

OTHER PUBLICATIONS

Paar et al., Understanding Cryptography, Oct. 2011, Springer; 1st ed. 2010 edition.*
Troncoso-Pastoriza et al., "Privacy Preserving Error Resilient DNA Searching Through Oblivious Automata," *CCS '07: Proceedings of the 14th ACM Conference on Computer and Communications Security*, pp. 519-528, 2007.
Blanton et al., "Secure Outsourcing of DNA Searching via Finite Automata," *DBSec '10: Proceedings of the 24th Annual IFIP WG 11.3 Working Conference on Data and Applications Security and Privacy*, pp. 49-64, 2010.
Jha et al., "Towards Practical Privacy for Genomic Computation," *Proceedings of the 2008 IEEE Symposium on Security and Privacy*, pp. 216-230, 2008.
Bruekers et al., "Privacy-Preserving Matching of DNA Profiles," *Tech. Rep.*, pp. 1-16, 2008.
Kantarcioglu et al., "A Cryptographic Approach to Securely Share and Query Genomic Sequences," *IEEE Transactions on Information Technology in Biomedicine*, vol. 12, No. 5, pp. 606-617, 2008.
Baldi et al., "Countering GATTACA: Efficient and Secure Testing of Fully-Sequenced Human Genomes," *CSS '11: Proceedings of the 18th ACM Conference on Computer and Communications Security*, pp. 691-702, 2011.
De Cristofaro et al., "GenoDroid: Are Privacy-Preserving Genomic Tests Ready for Prime Time?," *Proceedings of the ACM Workshop on Privacy in the Electronic Society—WPES*, pp. 97-108, 2012.
Canim et al., "Secure Management of Biomedical Data with Cryptographic Hardware," *IEEE Transactions on Information Technology in Biomedicine*, vol. 16, No. 1, pp. 166-175, 2012.
Homer et al., "Resolving Individuals Contributing Trace Amounts of DNA to Highly Complex Mixtures Using High-Density SNP Genotyping Microarrays," *PLoS Genetics*, vol. 4, Issue 8, pp. 1-9, 2008.
Gymrek et al., "Identifying Personal Genomes by Surname Inference," *Science*, vol. 339 (6117), pp. 321-324, 2013.
Zhou et al., "To Release or Not to Release: Evaluating Information Leaks in Aggregate Human-Genome Data," *ESORICS* 2011: *Proceedings of the 16th European Conference on Research in Computer Security*, pp. 607-627, 2011.
Chen et al., "Large-Scale Privacy-Preserving Mapping of Human Genomic Sequences on Hybrid Clouds," *NDSS '12: Proceeding of the 19th Network and Distributed System Security Symposium*, pp. 1-18, 2012.
Fienberg et al., "Privacy Preserving GWAS Data Sharing," *Proceedings of the 11$^{th}$ IEEE International Conference on Data Mining Workshops (ICDMW)*, pp. 628-635, 2011.
Wang et al., "Privacy-Preserving Genomic Computation Through Program Specialization," *Proceedings of the 16th ACM Conference on Computer and Communications Security*, pp. 338-347, 2009.
Goldreich et al., "Software Protection and Simulation on Oblivious RAMs," *J. ACM*, vol. 43, pp. 431-473, 1996.
Agrawal et al., "Order Preserving Encryption for Numeric Data," *Proceedings of the 2004 ACM SIGMOD International Conference on Management of Data*, pp. 563-574, 2004.
Boldyreva et al., "Order-Preserving Symmetric Encryption," *Proceedings of the 28th Annual International Conference on Advances in Cryptology: the Theory and Applications of Cryptographic Techniques*, pp. 224-241, 2009.
Popa et al., "CryptDB: A Practical Encrypted Relational DBMS," *Computer Science and Artificial Intelligence Laboratory Technical Report*, pp. 1-13, 2011.
Ayday et al., "Privacy-Preserving Processing of Raw Genomic Data," *Technical Report*, pp. 1-25, 2013.
Ayday et al., "Privacy-Enhancing Technologies for Medical Tests Using Genomic Data," *Technical Report*, pp. 1-16, 2012.
Boldyreva et al., "Order-Preserving Encryption Revisited: Improved Security Analysis and Alternative Solutions," *Proceedings of the 31st Annual Conference on Advances in Cryptology*, pp. 578-595, 2011.
International Search Report issued in PCT/EP2014/062736, dated Jan. 5, 2015.

* cited by examiner

Fig. 5

SEQUENCE LISTING

<160> NUMBER OF SEQ ID NOS: 4

<210> SEQ ID NO 1
<211> LENGTH: 290
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1
tagcccccac ccaacacaca cacacgtctt tttttctgaa tcatttgagt gtaccataca      60
tacgtcatgg ccctcagtgt atatttccta ggaattggga cattctctta cataaccaca    120
gtgcagttaa gggttccagg tattcacatt gatagaatgt gtatctaacc catggcccac    180
agttcagtgt ggtcaggtgc cctaacatcc tgtacagcac ttccccctct agtaccagag    240
ccagtctgga atcaaggatt gcatttactt ctaactcttt ggccctctg                290

<210> SEQ ID NO 2
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
agcatgttag ataagatagc tgtgctagta                                      30

<210> SEQ ID NO 3
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
atgtaaatgc tatgcgag                                                   18

<210> SEQ ID NO 4
<211> LENGTH: 18

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
tgctaaaggc tgatggca                                                    18
```

METHOD TO MANAGE RAW GENOMIC DATA IN A PRIVACY PRESERVING MANNER IN A BIOBANK

0 SEQUENCE LISTING

The instant application contains a Sequence Listing which has been submitted electronically in ASCII format and is hereby incorporated by reference in its entirety. Said ASCII copy, created on May 16, 2016, is named P49617_SL.txt and is 1,607 bytes in size.

1 INTRODUCTION

Genomics holds great promise for better predictive medicine and improved diagnoses. However, genomics also comes with a risk to privacy. The main threats to genomic data are (i) the revelation of an individual's genetic properties due to the leakage of his genomic data and (ii) the identification of an individual from his own genome sequence. For example, as part of a clinical trial, the genetic information of a patient, once leaked, could be linked to the disease under study (or to other diseases), which can have serious consequences such as denial of access to life insurance or to employment.

An increasing number of medical units (pharmaceutical companies or physicians) are willing to outsource the storage of genomes generated in clinical trials. As the medical unit would not own the genome, this is a good argument to convince clinical-trial participants to be sequenced and use their genomes to stratify clinical trials. Acting as a third party, a biobank could store patients' genomic data that would be used by the medical units for clinical trials. In the meantime, the patient can also benefit from the stored genomic information by interrogating his own genomic data, together with his family doctor, for specific genetic predispositions, susceptibilities and metabolical capacities. The major challenge here is to preserve the privacy of patients' genomic data while allowing the medical units to operate on specific parts of the genome (for which they are authorized).

Sequence alignment/map (SAM and its binary version BAM) files are the de facto standards used for all DNA sequence analyses produced by next-generation DNA sequencers. There are hundreds of millions of short reads (each including between 100 and 400 nucleotides) in the SAM file of a patient. Each nucleotide is present in several short reads in order to have high coverage of each patient's DNA. In the rest of this document, we present our work focusing on the SAM files, as it is clearer to present the proposed methods by using this human-readable format. However, the proposed scheme has no reliance on this particular format; our proposed algorithms can also be applied to other data formats that are used to store the raw genomic data (e.g., BAM).

In general, geneticists prefer storing aligned, raw genomic data of the patients (i.e., their SAM or BAM files), in addition to their variant calls (which include each nucleotide on the DNA sequence once, hence is much more compact). This is due to (i) the immaturity of bioinformatic algorithms and sequencing platforms, (ii) diseases that change the DNA sequence, and (iii) the rapid evolution of genomic research.

Bioinformatic algorithms for variant calling are currently not yet mature. Thus, the bioinformatic tools that geneticists require to assess the reliability of a variant call essentially necessitate keeping the read-level information available (e.g., in the SAM files). Moreover, DNA sequencing platforms are not error-free. For example, error rates for the commercially available DNA sequencing platforms, per nucleotide in a short read, are around 0.4% for the Illumina platforms, 1.78% for Ion Torrent and 13% for PacBio sequencing. Thus, geneticists prefer to observe each nucleotide in several short reads and to make conclusions based on the different values of a particular nucleotide in different short reads. Furthermore, if a patient carries a disease, which causes specific variations in the diseased cells (e.g., cancer), his DNA sequence in his healthy cells will be different from those diseased. Hence, when such a patient is sequenced from his diseased cells, it is crucial to store all his short reads, in addition to his variant calls. The short reads of such a patient involve both sequencing errors and mutations due to the corresponding disease, hence such mutations can be misclassified as sequencing errors by only looking at the patient's variant calls (rather than his short reads). Finally, the rapid evolution in the field of genomics produces new discoveries at a constantly accelerating pace, which cause significant advancements. Therefore, at this stage, geneticists do not know enough to decide which information should really be kept and what is superfluous, hence they prefer to store all outcome of the sequencing process as SAM files.

Today, most efforts on genomic privacy are focused on private string comparison (e.g., for paternity tests), private release of aggregate genomic data (e.g., for genetic researchers), and private clinical genomics (e.g., for private read mapping). However, none of the existing works address the issue of private processing of aligned, raw genomic data (i.e., SAM files), which is crucial to enable the use of genomic data in clinical trials. Therefore, in this application, we propose a privacy-preserving system for the storage, private retrieval and processing of the SAM files.

2.1 BRIEF DESCRIPTION OF THE INVENTION

According to the present invention, it is proposed a method to manage raw genomic data in a privacy preserving manner in a biobank, said raw genomic data comprising a plurality of aligned short reads, each aligned short read comprising a plurality of nucleotides and other fields comprising at least a position and a cigar string, said method comprising an encryption and storage stage comprising the steps of:

encrypting, for each short read, the position with an order preserving encryption algorithm, encrypting, for each short read, the cigar string with a symmetric encryption algorithm, encrypting the nucleotides with a stream cipher algorithm, storing all the encrypted data in the biobank together with a patient identification, the management of the raw genomic data comprising an access stage to the raw genomic data comprising the steps of:

receiving a request comprising a patient identification and at least one specific range of nucleotides, each range comprising a first and a second value allowing to determine the range, the first value being either the encrypted lower bound of the requested range of nucleotides or an adjusted encrypted adjusted lower bound in which the lower bound is included based on a maximum length of a short read, and the second value being the encrypted upper bound of the requested range of nucleotides, said first and second values having been encrypted with the order preserving encryption algorithm, in case that the first value is the encrypted lower bound, determining the encrypted adjusted lower bound in which the encrypted lower bound is included based on the maximum length of a short read, retrieving at least one short read having an encrypted position within the encrypted adjusted lower bound and the encrypted upper bound, decrypting the first and second values, in case that the first value is the encrypted adjusted lower bound, determining the lower bound with the adjusted lower bound and the maximum length of a short read, selectively masking the nucleotides of the at least one retrieved short read outside the range defined by the lower and upper bound, providing the selectively masked short read for further analysis.

In a nutshell, the proposed scheme privately stores the SAM files of the patients at a biobank. By using specific encryption techniques, it also provides the requested range of nucleotides (on the DNA sequence) to a medical unit, without revealing the locations of the short reads (which include the requested nucleotides) to the biobank. Furthermore, it prevents the leakage of extra information in the short reads to the medical unit by masking the encrypted short reads at the biobank.

That is, specific parts of the genomic data for which the medical unit is not authorized (or that the patient prefers to keep secret) are masked at the biobank, without revealing any information to the biobank. It is important to note that the proposed scheme enables the privacy-preserving processing of the SAM files both for individual treatment (when the medical unit is embodied in a physician) and for genetic research (when the medical unit is embodied in a pharmaceutical company). The main contributions of this invention are summarized in the following:

1. We develop a privacy-preserving framework for the retrieval of encrypted short reads (in the SAM files) from the biobank without revealing the scope of the request to the biobank.

2. We develop an efficient system for obfuscating (i.e., masking) specific parts of the encrypted short reads (which include the nucleotides requested by a medical unit) at the biobank before providing them to the medical unit.

3. We show the benefit of masking by evaluating the information leak to the medical unit, with and without the masking is in place.

Alignment is with respect to the reference genome, which is assembled by the scientists as a representative example of the set of genes.

4. We implement the proposed privacy-preserving system by using real genomic data, evaluate its efficiency, and show its practicality.

2.2 RELATED WORK

We can put the research on genomic privacy in three main categories: (i) private string searching and comparison, (ii) private release of aggregate data, and (iii) private clinical genomics.

Troncoso-Pastoriza et al. (J. R. Troncoso-Pastoriza, S. Katzenbeisser, and M. Celik, "Privacy preserving error resilient DNA searching through oblivious automata," CCS '07: Proceedings of the 14th ACM Conference on Computer and Communications Security, 2007) propose a protocol for string searching (using a finite state machine), which is then re-visited by Blanton and Aliasgari (M. Blanton and M. Aliasgari, "Secure outsourcing of DNA searching via finite automata," DBSec'10: Proceedings of the 24th Annual IFIP WG 11.3 Working Conference on Data and Applications Security and Privacy, pp. 49-64, 2010). To compute the similarity of DNA sequences, Jha et al. (S. Jha, L. Kruger, and V. Shmatikov, "Towards practical privacy for genomic computation," Proceedings of the 2008 IEEE Symposium on Security and Privacy, pp. 216-230, 2008) propose techniques for privately computing the edit distance of two strings by using garbled circuits. Bruekers et al. (F. Bruekers, S. Katzenbeisser, K. Kursawe, and P. Tuyls, "Privacy-preserving matching of DNA profiles," tech. rep., 2008) propose a privacy-enhanced comparison of DNA profiles by using homomorphic encryption. Kantarcioglu et al. (M. Kantarcioglu, W. Jiang, Y. Liu, and B. Malin, "A cryptographic approach to securely share and query genomic sequences," IEEE Transactions on Information Technology in Biomedicine, vol. 12, no. 5, pp. 606-617, 2008) propose using homomorphic encryption to perform scientific investigations on integrated genomic data. In one of their recent works, Baldi et al. (P. Baldi, R. Baronio, E. De Cristofaro, P. Gasti, and G. Tsudik, "Countering GATTACA: Efficient and secure testing of fully-sequenced human genomes," CCS '11: Proceedings of the 18th ACM Conference on Computer and Communications Security, pp. 691-702, 2011) make use of both medical and cryptographic tools for privacy-preserving paternity tests, personalized medicine, and genetic compatibility tests. Then, in their follow-up work, De Cristofaro et al. propose an implemented toolkit, called GenoDroid (E. De Cristofaro, S. Faber, P. Gasti, and G. Tsudik, "Genodroid: Are privacy-preserving genomic tests ready for primetime?," Proceedings of the ACM workshop on Privacy in the electronic society—WPES, pp. 97-108, 2012). Finally, instead of using public key encryption, Canim et al. (M. Canim, M. Kantarcioglu, and B. Malin, "Secure management of biomedical data with cryptographic hardware," IEEE Transactions on Information Technology in Biomedicine, vol. 16, no. 1, 2012) propose securing the biomedical data by using cryptographic hardware.

When releasing databases consisting of aggregate genomic data, it is shown that known privacy-preserving approaches (e.g., de-identification) are ineffective on (unencrypted) genomic data. Homer et al. (N. Homer, S. Szelinger, M. Redman, D. Duggan, and W. Tembe, "Resolving individuals contributing trace amounts of DNA to highly complex mixtures using high-density SNP genotyping microarrays," PLoS Genetics, vol. 4, August 2008) prove that the presence of a specific individual in a case group can be determined. In another recent study, Gymrek et al. (M. Gymrek, A. L. McGuire, D. Golan, E. Halperin, and Y. Erlich, "Identifying personal genomes by surname inference," Science: 339 (6117), January 2013) report that they exposed the identity of 50 individuals whose DNA was donated anonymously for scientific study through consortiums such as the 1000 Genomes Project. Zhou et al. (X. Zhou, B. Peng, Y. F. Li, Y. Chen, H. Tang, and X. Wang, "To release or not to release: Evaluating information leaks in aggregate human-genome data," ESORICS'11: Proceedings of the 16th European Conference on Research in Computer Security, pp. 607-627, 2011) study the privacy risks of releasing the aggregate genomic data. Recently, the use of differential privacy has been proposed by Fienberg et al. (S. E. Fienberg, A. Slavkovic, and C. Uhler, "Privacy preserving GWAS data sharing," Proceedings of the IEEE 11th International Conference on Data Mining Workshops (ICDMW), December 2011) to ensure that two aggregated genomic databases have indistinguishable statistical features.

Utilizing a public cloud, Chen et al. (Y. Chen, B. Peng, X. Wang, and H. Tang, "Large-scale privacy-preserving mapping of human genomic sequences on hybrid clouds," NDSS'12: Proceeding of the 19th Network and Distributed System Security Symposium, 2012) propose a secure and efficient algorithm to align short DNA sequences to a reference DNA sequence. Furthermore, Wang et al. (R. Wang, X. Wang, Z. Li, H. Tang, M. K. Reiter, and Z. Dong, "Privacy-preserving genomic computation through program specialization," Proceedings of the 16th ACM Conference on Computer and Communications Security, pp. 338-347, 2009.) propose a privacy-protection framework for important classes of genomic computations (e.g., search for homologous genes).

As we discussed before, none of the aforementioned efforts on genomic privacy focus on the processing of aligned, raw genomic data. Therefore, in this work, we focus on private storage, retrieval, and processing of raw genomic data.

2.3 BRIEF DESCRIPTION OF THE FIGURES

The present invention will be better understood thanks to the attached figures in which:

FIG. 1 illustrates the format of the short read min a SAM file (SEQ ID NO: 1), FIG. 2 illustrates the content of a short read (SR) (SEQ ID NO: 3) and its Cigar String (CS) with respect to the reference genome (SEQ ID NO: 2), FIG. 3 illustrates parts to be masked in the short reads for out-of-range content, FIG. 4 illustrates parts to be masked in a short read based on patient's consent, FIG. 5 illustrates an example for the encryption, masking and decryption of the content of the short read (SR) that was first introduced in FIG. 2 (SEQ ID NOS: 3 and 4, respectively, in order of appearance).

3 GENOMIC BACKGROUND

3.1 SAM Files

Figure 1:
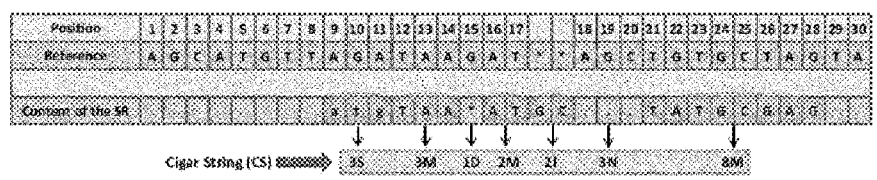

The DNA sequence data produced by next-generation DNA sequencing consists of millions of short reads, each typically including between 100 and 400 nucleotides (A,C, G,T), depending on the type of sequencer. These reads are randomly sampled from a human genome. Each read is then bio-informatically treated and positioned (aligned) to its genetic location to produce a so-called SAM file. There are hundreds of millions of aligned short reads in the SAM file of one patient. In FIG. 1, we illustrate the format of a short read in a SAM file. The numbers and letters after the content in FIG. 1 represent the sequencing quality of the nucleotides in the content.

The privacy-sensitive fields of a short read are (i) its position with respect to the reference genome (digital nucleic acid sequence database, assembled by scientists as a representative example of a species' set of genes), (ii) its cigar string (CS), and (iii) its content (including the nucleotides from $\{A, T, G, C\}$). For the simplicity of the presentation, from here on, we focus on these three fields only. We note that the rest of the short read does not contain privacy sensitive information about the patient, hence the rest of the short read can be encrypted as a vector and provided to the medical unit, along with the aforementioned privacy-sensitive fields.

Figure 2:
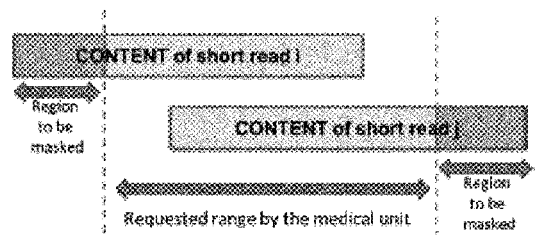

The position of a short read denotes the position of the first aligned nucleotide in its content, with respect to the reference genome. The short read might have additional nucleotides that are not in the reference or it might be missing nucleotides that are in the reference. The cigar string (CS) of a short read expresses these variations in the content of the short read. The CS includes pairs of nucleotide lengths and the associated operations. The operations in the CS indicate some properties about content of the short read such as which nucleotides align with the reference, which are deleted from the reference, and which are insertions that are not in the reference. We illustrate descriptions of common operations in the CS in Table 1. Finally, the content of a short read includes the nucleotides. In FIG. 2, we illustrate how the content of a short read looks and how the CS of the corresponding short read is generated. The actual content only includes nucleotides; the dots (at positions 18-20) and star (at position 15) in FIG. 2 are not present in the content, and they are understood from the CS of the short read.

TABLE 1

Operations in the Cigar String (CS) of a short read.

| Operation | Description |
|---|---|
| M | alignment match (can be a sequence match or mismatch) |
| I | insertion to the reference |
| D | deletion from the reference |
| N | skipped region from the reference |
| S | soft clipping (misalignment), clipped sequences (i.e., misaligned nucleotides) present in the content |
| H | hard clipping (misalignment), clipped sequences (i.e., misaligned nucleotides) NOT present in the content |
| P | padding (silent deletion from padded reference) |

3.2 Single Nucleotide Polymorphism (SNP)

There are several types of DNA variations in the human genome, among which the single nucleotide polymorphism (SNP) is the most common. A SNP is a position in the genome holding a nucleotide that varies between individuals. Recent discoveries show that the susceptibility of a patient to several diseases can be computed from his SNPs. Thus, we also consider the SNPs of a patient when evaluating the information leakage in Section 8.

SNP positions might carry a different nucleotide than the reference genome. For example, in the short read in FIG. 2, position 22 can be a SNP position, because, even though there is an alignment match between the short read and the reference genome, the nucleotide in the short read is different from the reference.

4 OVERVIEW OF THE PROPOSED SOLUTION

In this case, we develop a privacy-preserving system for the storage, retrieval and processing of the SAM files.

In the FIG. 2, the position of the short read corresponds to the first aligned nucleotide in its content and it is 12 in this example. The CS of the short read includes 7 pairs, each indicating an operation from Table 1 and the number of nucleotides involved in the corresponding operation. The non-aligned nucleotides (the nucleotides represented with the operation "S" in the CS are represented in lowercase letters (i.e., a). The dots (at positions 18-20) and star (at position 15) represent a skipped region and a deletion in the SR, respectively, and they are not present in the actual content.

Each part (location, CS, and content) of each short read (in the SAM file) is encrypted (via a different encryption scheme) after the sequencing, and encrypted SAM files of the patients are stored at a biobank.

We assume that SAM files are stored at the biobank by using patient identification or pseudonyms; this way, the biobank cannot associate the conducted genetic tests (if it knows the type of the conducted test) and the medical unit (MU), which conducts these tests, with the real identities of the patients. We note that a private company (e.g., cloud storage service), the government, or a non-profit organization could play the role of the biobank.

The cryptographic keys of the patients are stored using one of the following approaches: (i) The patient's cryptographic keys are stored on a patient's device (e.g., smart card or a smart phone), or (ii) the patient's cryptographic keys are stored on a key manager by using the patient's identification. In the former approach, operations involving the patient are done on the MU's (e.g., the pharmaceutical company or the physician) computer via the patient's device, hence this approach requires the involvement of the patient in the operation (e.g., physical presence at the physician). Whereas, the latter approach does not require the participation of the patient in the protocol. From here on, we assume the existence of a masking and key manager (MK) in the system to store cryptographic keys of the patients. The MK can also be embodied in the government or a private company. The proposed scheme can be formulated similarly for the patient's device. In the following, we briefly discuss the private retrieval and masking of the short reads (details are in Section 7).

4.1 Private Retrieval of the Short Reads

When the MU requests a specific range of nucleotides (on the DNA sequence of one or multiple patients), the biobank provides all the short reads that include at least one nucleotide from the requested range through the MK. During this process, the patient does not want to reveal his complete genome to the MU, to the biobank, or to the MK. Furthermore, it is not desirable for the biobank to learn the requested range of nucleotides (as the biobank can infer the nature of the genetic test from this requested range). Thus, we develop a privacy-preserving system for the retrieval of the short reads by the MU. The proposed scheme provides the short reads that include the requested range of nucleotides to the MU without revealing the positions of these short reads to the biobank.

To achieve this goal, we use order preserving encryption (OPE) on the positions of the short reads (in the SAM file). OPE is a deterministic encryption scheme whose encryption function preserves numerical ordering of the plaintexts. Thus, OPE enables the encryption of the positions of the short reads and preserves the numerical ordering of the plaintext positions.

4.2 Masking of the Short Reads

We prevent the leakage of extra information in the short reads to the MU by masking the encrypted short reads at the biobank (before sending them to the MU). As each short read includes between 100 and 400 nucleotides, some provided short reads might include information out of the MU's requested (or authorized) range of genomic data, as in FIG. 3. Similarly, some provided short reads might contain privacy-sensitive SNPs of the patient (which would reveal the patient's susceptibilities to privacy-sensitive diseases such as Alzheimer's), hence the patient might not give consent to reveal such parts, as in FIG. 4. From here on, the nucleotides that the patient does not consent to reveal will be referred to as the non-consented nucleotides.

To achieve this goal, we use stream cipher (SC) encryption on the contents of the short reads (in the SAM file) and mask certain parts of the encrypted short reads at the biobank, without decrypting them. In brief, the MK marks particular parts of the requested shorts reads (which are retrieved by the biobank as discussed before) for masking, based on the patient's consent (the patient provides his consent to the MU for the genetic test and his consent is provided to the MK by the MU in a pseudonymized form) and the boundaries of the requested range of nucleotides. Thus, the MK creates masking vectors and passes them to the biobank. Then, the biobank executes the masking on the previously retrieved (encrypted) short reads by using these masking vectors and sends them to the MU, where the short reads are decrypted and used for genetic tests. It is important to note that after the short reads are decrypted at the MU, the MU is not able to determine the nucleotides at the masked positions.

5 DESIGN CONSTRAINTS AND OPTIONS

Here, we briefly discuss some alternative design options. For security, efficiency, and availability, we propose storing the SAM files at a biobank instead of at the MU. Extreme precaution is needed for the storage of genomic data due to its sensitivity. We assume that the biobank is more "security-aware" than a MU, hence it can protect the stored genomic data against a hacker better than a MU (yet, attacks against the biobank cannot be ruled out, as we discuss next). Indeed, this assumption is supported by recent serious medical data breaches from various MUs (e.g., Howard University Hospital and TRICARE, which handles health insurance for the US military). Furthermore, by storing the SAM files at one biobank, multiple MUs can access the patients' genomic data from it (instead of each MU individually storing that same large amount of data). Finally, the genomic data of the patient should be available any time to any MU (e.g., for emergencies), thus it should be stored at a reliable centralized storage.

It can be argued that the genomic data can be stored on a patient's computer or mobile device, instead of the biobank. However, we assert that this should be avoided for the following reasons: On one hand, as we discussed before, genomic data of the patient should be available any time, thus it should be stored at a reliable source such as the biobank. On the other hand, leaving the patient's genomic data in his own hands and letting him store it on his computer or mobile device is risky, because his mobile device can be stolen or his computer can be hacked. It is true that the patient's cryptographic keys (or his authentication material) to access his genomic data at the biobank can also be stolen. But, in the case of a stolen cryptographic key, his genomic data (which is stored at the biobank) will still be safe as the patient can notify the biobank to block access to his genomic data in such a scenario. It can also be assumed that the biobank authenticates the patient's access to his genomic data by using biometric authentication tools; the use of such tools would make it even harder for an attacker to compromise the genomic data of the patient.

In the present method, this work, we use OPE instead of private information retrieval (PIR) or oblivious RAM (O-RAM) storage [see O. Goldreich and R. Ostrovsky, "Software protection and simulation on oblivious RAMs," J. ACM, vol. 43, pp. 431-473, May 1996) techniques for the private retrieval of the short reads for the two following reasons: (i) Efficient PIR techniques either assume multiple, non-colluding servers (biobanks) holding copies of the entire database (which is not desirable in our case, as the size of the genomic data is already very large) or provide more information (to the MU) than it is authorized in order to confuse the server (biobank). And (ii) although O-RAM techniques completely hide the data access patterns from the server (biobank), even the most efficient implementations of O-RAM introduces high storage overhead to the client (patient) and introduces about 25 times more overhead with respect to non-oblivious storage.

6 THREAT MODEL AND SECURITY CONSIDERATIONS

We consider the following models for the attacker:
- A curious party at the biobank (or a hacker who breaks into the biobank), who tries (i) to infer the genomic sequence of a patient from his stored genomic data and (ii) to associate the type of the genetic test (e.g., the disease for which the patient is being tested, which can be inferred from the nucleotides requested by the MU) with the patient being tested.
- A curious party at the MK (or a hacker who breaks into the MK), who tries (i) to infer the genomic sequence of a patient from his stored cryptographic keys and the information provided by the biobank and (ii) to associate the type of the genetic test with the patient being tested.
- A malicious party at the MU, who can be considered either as an attacker who hacks into the MU's system or a disgruntled employee who has access to the MU's database. The goal of such an attacker is to obtain the private genomic data of a patient for which it is not authorized.

Apart from (potentially) being curious, we assume that the biobank and the MK are honest organizations.

That is, the biobank and the MK honestly follow the protocols and provide correct information to the other parties. In the following, we discuss how we prevent the aforementioned attacks.

SAM files are encrypted and stored at the biobank to avoid the biobank from inferring the genomic data of the patients. To avoid the biobank from associating the conducted genetic tests with the patients, we hide both the real identities of the patients (using pseudonyms) and the types of the conducted tests (using OPE on the positions of the short reads) from the biobank. If the biobank learns the requested range of nucleotides by a MU, it can infer the type of the genetic test (e.g., the disease for which the patient is being tested). Thus, even though the real identities of the patients are hidden from the biobank, knowing the MU (e.g., the name of the hospital), the biobank can de-anonymize a victim using other sources (e.g., by associating the time of the test and the location of the MU with the location patterns of the victim), hence associate the conducted genetic test with the victim. For the same reason (i.e., to avoid the MK from associating the genetic tests with the patients), we do not reveal the real identities of the MUs or the real identities of the patients to the MK. Thus, for each genetic test, the MK only learns the requested range of nucleotides and the pseudonyms of the patient and the MU. The MK can infer the type of the conducted genetic test from the requested range of nucleotides, but the aforementioned de-anonymization attack is not possible, as the MK does not know the real identities of the MUs.

Furthermore, the MK cannot infer the genomic data of the patients by using the information it receives from the biobank and the cryptographic keys it stores. As we will discuss in Section 7.2, we only provide the positions and the cigar strings (CSs) of a subset of the short reads (depending on the range of nucleotides requested by the MU) to the MK, which is not enough to infer the nucleotides residing in the contents of corresponding short reads (the contents of the short reads are never transferred to the MK).

A potential attacker at the MU can learn about a patient's susceptibilities to privacy-sensitive diseases if he obtains specific SNPs of the patient. As we mentioned in Section 4, by masking the encrypted short-reads before providing them to the MU, we avoid the MU acquiring more genomic data than it is authorized for.

Finally, as the patient is not involved in the protocol, his genomic privacy can be compromised in the case of collusion between other parties (i.e., the biobank, the MK, and the MU). That is, if the biobank colludes with the MK, the short reads of the patient would be revealed and the genetic test (conducted by the MU) can be associated with the patient. Other collusion possibilities (between the biobank and the MU or between the MU and the MK) would let the biobank (or MK) associate the genetic test with the patient.

We note that if the patient actively participates in the protocols via his smart card or mobile device (instead of the MK), the collusion between the other parties would not compromise the privacy of the patient.

Figure 5:
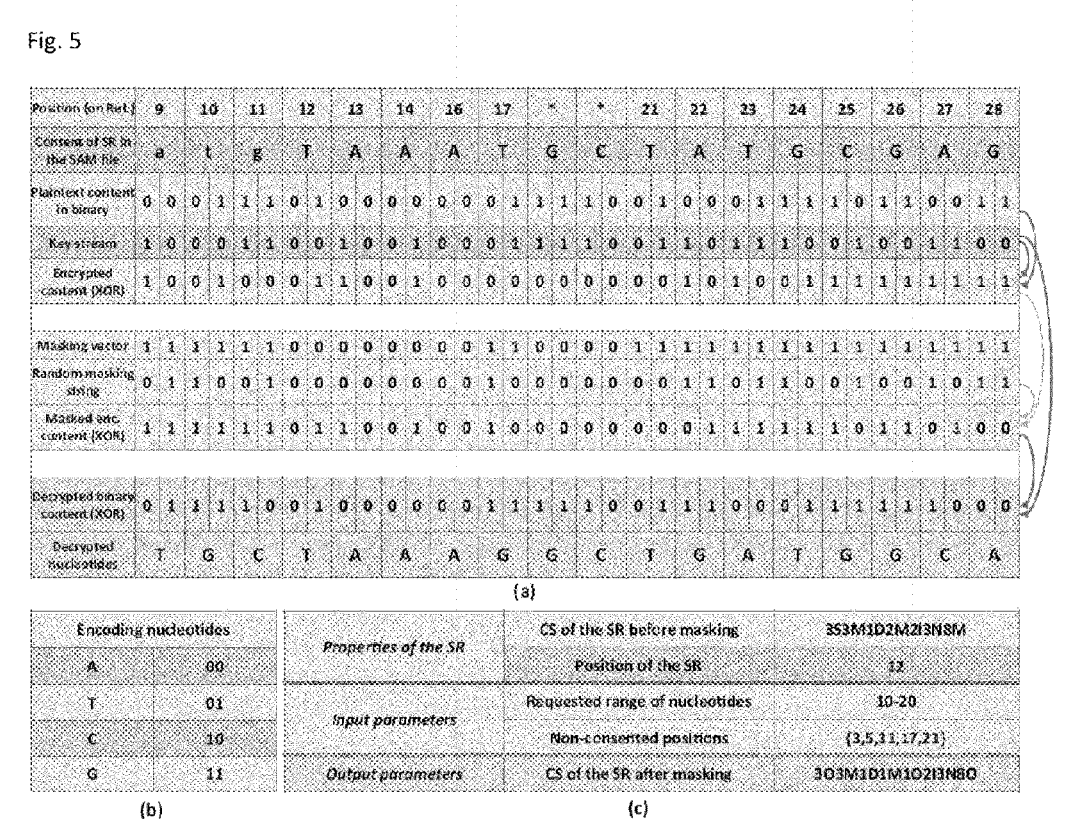

The FIG. 5 is an illustrative example for the encryption, masking and decryption of the content of the short read (SR) that was first introduced in FIG. 2. The arrows on the right show the inputs of the corresponding XOR operation. (a) Content of the SR (the 2 stars between positions 17 and 21 represent the positions at which the SR has insertions, G and C), its binary representation (following the encoding in (b)), the key stream to encrypt the corresponding content, and the format of the encrypted content (after the binary plaintext content is XOR-ed with the key stream). Furthermore, following the discussion in Section 7.2, we illustrate the masking vector generated at the MK considering the range of the requested nucleotides and the patient's consent (in (c)), the random masking string for the corresponding masking vector, and the format of the masked content (generated by XOR-ing the encrypted content with the random masking string). Finally, we show the format of the decrypted binary content, and the corresponding decrypted nucleotides. (b) Encoding format of the nucleotides A, T, C, and G. (c) Properties of the corresponding short read, requested range of nucleotides by the MU, non-consented nucleotides by the patient, and format of the CS after masking.

7 PRIVACY-PRESERVING PROCESSING OF RAW GENOMIC DATA

7.1 Cryptographic Keys and Encryption of the Short Reads

The different parts of each short read are encrypted as follows: (i) The positions of the short reads are encrypted using order preserving encryption (OPE), (ii) the cigar string (CS) of each short read is encrypted using a semantically secure symmetric encryption function (SE), and (iii) the content of each short read, i.e. the nucleotides, is encrypted using a stream cipher (SC). We note that an SC also provides semantic security, and although we really need an SC for the encryption of the content, one can also use an SC for the encryption of the CS (we use an SC both for the encryption of the content and the CS in our implementation). We represent the key used for the semantically secure encryption scheme between two parties i and j as $K_{i,j}$. The symmetric OPE key that is used to encrypt the positions of the short reads of patient P is represented as $K_P^O$. Further, the master key of patient P, which is used to generate the keys of the SC is represented as $M_P^O$. We denote $K_P^{C_i}$ as the SC key used to encrypt the content of the short read whose position is $L_i$. We compute $K_P^{C_i}=H(Mp,F(L_i,S_i),L_i)$ where $L_i$ is the (starting) position of the corresponding short read (on the DNA sequence), $S_i$ is a random salt to provide different keys for the short-reads with the same positions, and H is a pseudorandom function. Furthermore, $F(L_i,S_i)$ is a function that generates a nonce from the position and the random salt of the corresponding short read. We note that the random salts of the short reads are stored in plaintext.

We assume that the certified institution (CI), where the patient's DNA is sequenced and analyzed, has $K_P^O$, $M_P$, and $K_{P,Ci}$ ($K_{P,Ci}$ is used to encrypt the CSs of the short reads) for the initial encryption of the patient's genomic data. These keys are then deleted from the CI after the sequencing, alignment, and encryption. We also assume that the patient's cryptographic keys for symmetric encryption, OPE, and SC are stored at the MK, and the patient does not participate in the protocol (except for giving his consent). If the patient participates in the protocols, his keys are stored on his device (e.g., smart phone) and operations are done via that device, instead of the MK. Thus, for patient P, the MK stores, $K_P^O$, $M_P$, and $K_{P,Ci}$. Using $M_P$, the MK generates the decryption keys required by the SC and sends them to the MU (through the biobank). Finally, the MU only stores the public key of the MK, $\kappa_{MK}$.

Figure 6:
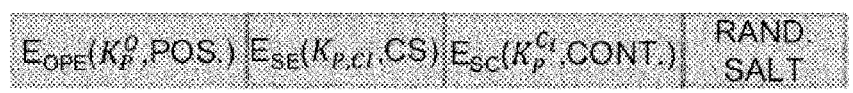
FIG. 6 illustrates the Format of an encrypted short read.

We represent the public-key encryption of message m under the public key of i as $\varepsilon(\kappa_i,m)$, the encryption of message m via a semantically secure symmetric encryption function (SE), using the symmetric key between i and j as $E_{SE}(K_{i,j},m)$, and the OPE of message m using the OPE key of P as $E_{OPE}(K_P^O,m)$. Furthermore, we represent the SC encryption of the content of a short read as $E_{SC}(K_P^{C_i},C_i)$, where $C_i$ represents the content of the short read at $L_i$. In FIG. 5(a), we illustrate how the content of a short read is translated to plaintext bits and encrypted using SC (by XOR-ing the content with the key stream). Finally, in FIG. 6, we illustrate the format of an encrypted short read. The size of each field is discussed in Section 9.

7.2 Practical Example

Figure 7A:
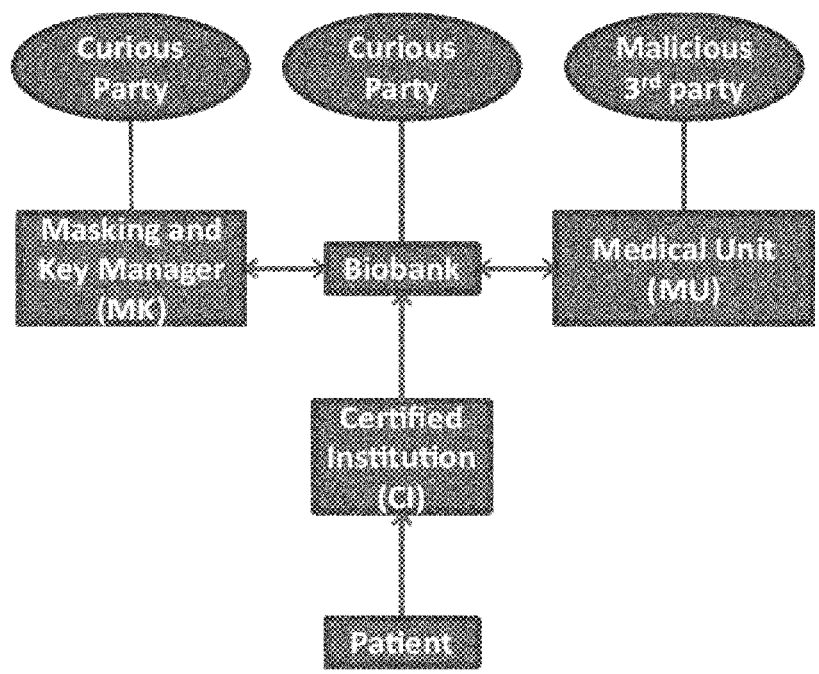
FIG. 7a illustrates the connections between the parties in the proposed protocol.
Figure 7B:
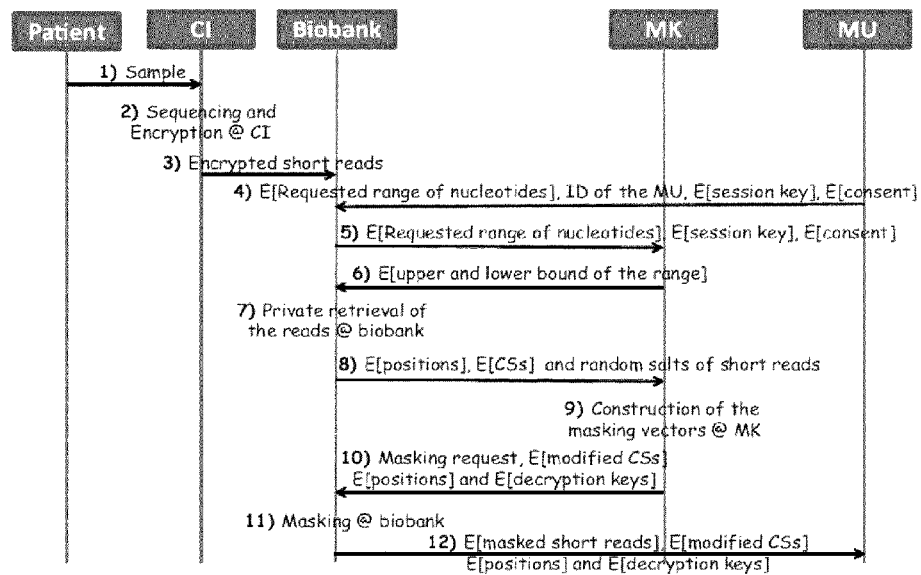
FIG. 7b illustrates the operations and message exchanges in the proposed protocol.

Typically, the MU requests a range of nucleotides (on the DNA sequence of one or more patients) from the biobank (either for a personal genetic test or for clinical research). For simplicity of the presentation, we assume that the request is for a specific range of nucleotides of patient P. We note that when the MU is embodied in a pharmaceutical company, the MU does not know the real identities of the patients (i.e. participants of the clinical trial). Thus, in this case, the MU asks for a certain range of nucleotides of several pseudonymized patients from the biobank, who consented to participate in the corresponding clinical trial (the pseudonyms of these patients are known by the MU or by the biobank, and the general consent for the corresponding clinical trial is forwarded to the MK for masking). We illustrate the connections between the parties that are involved in the protocol in FIG. 7(a). In the following, we describe the steps of the proposed protocol (these steps are also illustrated in FIG. 7(b)).

Step 1: The patient (P) provides a sample (e.g., his saliva) along with his consent to the certified institution (CI) for sequencing. We assume that laws prevent DNA sequencing of a (stolen) biological sample (e.g., hair) without the patient's consent.

Step 2: The sample is sequenced by the CI. Next, the CI aligns the shorts reads of the patient with respect to the reference genome and constructs the SAM file of the patient. The short reads of the patient are also encrypted at the CI (as discussed in Section 7.1).

Step 3: The CI sends the encrypted SAM file to the biobank along with the corresponding pseudonym of the patient. We note that the first 3 steps of the protocol are executed only once.

Step 4: The MU generates a one-time session key $K_{MK,MU}$, which will be used for the secure communication between the MU and the MK (as we do not reveal the real identity of the MU to the MK, as discussed in Section 6, this key is generated for each session). The MU encrypts this session key with the public key of the MK to obtain $\varepsilon(\kappa_{MK},K_{MK,MU})$.

Next, the MU requests all short reads of patient P, which include nucleotides from the range $[R_L,R_U]$ on the DNA sequence ($R_L$ being the lower bound and $R_U$ being the upper bound of the requested range) for a genetic test. The MU encrypts the lower and upper bounds of the requested range with $K_{MK,MU}$ to obtain $E_{SE}(K_{MK,MU},RL\|RU)$ and sends the corresponding request to the biobank along with a least the pseudonym or identification of the patient P and the encrypted requested range. Other data can be included into the request such as the identification of the MU, $\varepsilon(K_{MK},K_{MK,MU})$, and $E_{SE}(K_{MK,MU},\Omega_P)$, where P is the pseudonymized consent of the patient. We note that an access control unit will store the authorizations (i.e., access rights) of the MU to different parts of the genomic data. These access rights of different MUs to the SAM files are defined either jointly by the MU and the patient or by the medical authorities. In our setting, the access control unit can be the biobank (or a medical authority), and the biobank can provide the access rights of the corresponding MU to the MK without revealing the real identity of the MU; hence the MK uses these access rights (along with the pseudonymized consent P) to generate the masking vectors (as in Step 9).

Step 5: The biobank forwards $E_{SE}(K_{MK,MU},RL\|RU)$ and $E_{SE}(K_{MK,MU},\Omega_P)$, along with the pseudonym of the patient, the encrypted session key $\varepsilon(\kappa_{MK},K_{MK,MU})$, and the access rights of the corresponding MU to the MK.

Step 6: The MK decrypts the session key to obtain $K_{MK,MU}$. Then, it decrypts the request ($E_{SE}(K_{MK,MU},RL\|RU)$) computes the encrypted range $[E_{OPE}(K_P^O,(R_L-\Gamma)),E_{OPE}(K_P^O,R_U)]$, and sends this encrypted range to the biobank (with the pseudonym of P). As we discussed before, the position of a short read is the position of the first aligned nucleotide in its content. Let Γ be the maximum number of nucleotides in a short read. Then, the short reads with position in $[R_L-\Gamma, R_L-1]$ (named adjusted short read) might also include nucleotides from the requested range ($[R_L, R_U]$) in their contents. Thus, the MK re-defines the lower bound to obtain the adjusted lower bound defining an adjusted range in which the lower bound in included of the request as $R_L-\Gamma$ in order to make sure that all the short reads (which include at least one nucleotide from the requested range of nucleotides) are retrieved by the biobank (as opposed to the lower bound, the MK does not need to re-define the upper bound of the request).

As stated above, Γ is the maximum number of nucleotides in a short read (maximum length of a short read determined by the output of the sequencer). We redefine the lower bound and compute the adjusted lower bound as the position of the nucleotide that is indicated in the lower bound of the request minus the maximum length of a short read ($R_L-\Gamma$) in order to make sure that all the short reads (which include at least one nucleotide from the requested range of nucleotides) are retrieved by the biobank.

Step 7: The biobank retrieves all the short reads (in the SAM file of patient P) whose encrypted positions ($E_{OPE}(K_P^O, L_i)$) is in $[E_{OPE}(K_P^O, (R_L-\Gamma)), E_{OPE}(K_P^O, R_U)]$, and constructs the set $\Delta = \{E_{OPE}(K_P^O, L_i): E_{OPE}(K_P^O, (R_L-\Gamma)) \leq E_{OPE}(K_P^O, L_i) \leq E_{OPE}(K_P^O, R_U)\}$. As OPE preserves the numerical ordering of the plaintext positions, the biobank constructs the set $\Delta$ without accessing the plaintext positions of the short-reads.

Step 8: The biobank provides the encrypted positions in $\Delta$ along with the corresponding encrypted CSs and the random salt values of the short reads to the MK.

Step 9: The MK decrypts the corresponding positions and the CSs of the retrieved short reads by using $K_P^O$ and $K_{P,CI}$ in order to construct the masking vectors for the biobank.

These masking vectors correspond to the nucleotides outside the range, and prevent the leakage of out-of-range content (in FIG. 3) and non-consented nucleotides (in FIG. 4) to the MU, as we discussed in Section 4.2.

Using the position and the CS of a short read, the MK can determine the exact positions of the nucleotides in the content of a short read (but not the contents of the nucleotides, because the contents are encrypted and stored at the biobank). Using this information, the MK can determine the parts in the content of the short read that are out of the requested range $[R_L, R_U]$. Furthermore, the MK can also determine whether the short read includes any nucleotide positions for which the patient P does not give consent to the MU (the patient's pseudonymized consent, $\Omega_P$, is provided to the MK in Step 5) or the MU is not authorized due to lack of its access rights. Therefore, the MK constructs binary masking vectors indicating the positions in the contents of the short reads that are needed to be masked by the biobank before sending the retrieved short reads to the MU.

Let $H\Pi_P$ be the set of nucleotide positions (on the DNA sequence) for which the patient P does not give consent to the MU (e.g., set of positions including privacy-sensitive SNPs of the patient). Then, assuming that the MU has the access rights (defined by the access control unit as discussed in Step 4) to the requested range $[R_L, R_U]$, the set $\Sigma = [R_L, R_U] \setminus \Pi_P$ includes the positions of the nucleotides that can be provided to the MU without masking. The masking vector for a short read (with position $L_i$) is constructed following Algorithm 1.

---

Algorithm 1 Construct the masking vector
$V_m$ for short read with position $L_i$

---

Require: $L|_i$, CS of the short read at $L_i$, Positions of authorized nucleotides ($\Sigma$)
Ensure: $V_m$ {Each nucleotide is represented by 2-bits, initially all bits are set to 0}
1: $N_p \leftarrow$ # pairs in the CS of the short read
2: $P_0 \leftarrow L_i$ {Assign the position of the short read to $P_0$}
3: $I \leftarrow 0$ {Index of the nucleotides in the content of the short read}
4: for $i \leftarrow 1$ to $N_p$ do
5:     Get the $i^{th}$ pair of the CS with the fields $n_i$ and $l_i$
6:     $l_i \leftarrow$ Operation noted in the $i^{th}$ pair of the CS (from Table 1)
7:     $n_i \leftarrow$ # nucleotides following the operation noted in $l_i$
8:     if $l_i = H \vee l_i = P$ then
9:         do nothing
10:    else if $l_i = S$ then
11:       for $j \leftarrow 0$ to $(n_i - 1)$ do
12:           $V_m(1, 2(I + j)) \leftarrow 1$, $V_m(1, 2(I + j) + 1) \leftarrow 1$ {Mark the $(I + j)^{th}$ nucleotide in the content of the short read for masking}
13:       end for
14:       $I \leftarrow I + n_i$
15:    else if $l_i = M$ then
16:       for $j \leftarrow 0$ to $(n_i - 1)$ do
17:         if $(P_0) \notin \Sigma$ then
18:           $V_m(1, 2(I + j)) \leftarrow 1$, $V_m(1, 2(I + j) + 1) \leftarrow 1$
19:         end if
20:         $P_0 \leftarrow P_0 + 1$
21:       end for
22:       $I \leftarrow I + n_i$
23:    else if $l_i = I$ then
24:       if $(P_0) \notin \Sigma$ then
25:         for $j \leftarrow 0$ to $(n_i - 1)$ do
26:           $V_m(1, 2(I + j)) \leftarrow 1$, $V_m(1, 2(I + j) + 1) \leftarrow 1$
27:         end for
28:       end if
29:       $I \leftarrow I + n_i$
30:    else if $l_i = D \vee l_i = N$ then
31:       $P_0 \leftarrow P_0 + n_i$
32:    end if
33: end for

---

FIG. 5(a), we illustrate how the masking vector is constructed for the corresponding short read, when the requested range of nucleotides is [10, 20] and for a given $\Pi_P$ (as in FIG. 5(c)).

The MK also modifies the CS of each short read (if it is marked for masking) according to the nucleotides to be masked. That is, the MK modifies the CS such that the masked nucleotides are represented with a new operation "O" in the CS. Alternatively, the consent of the patient can be used by the MU instead of modifying the CS. Thus, the MU determines the masked nucleotides from the consent. By doing so, when the MU receives the short reads (which include the requested nucleotides), it can see which parts of them are masked (hence which parts of them it needs to discard for its research purposes). In FIG. 5(c), we illustrate how the CS of the corresponding short read changes as a result of the masking vector in FIG. 5(a). Then, the MK generates the decryption keys for each short read (whose position is in $\Delta$) by using the master key of the patient ($M_P$), positions of the shorts-read, and the random salt values. The generation of the decryption keys for the SC is the same as the generation of the encryption keys as we discussed in Section 7.1

Step 10: The MK encrypts the positions, the (modified) CSs, and the generated decryption keys of the contents of the short reads using $K_{MK,MU}$. Then, it sends the masking vectors along with the encrypted positions, CSs and decryption keys to the biobank.

---
Algorithm 2 Construct the random masking string $V_s$ and conduct the masking for short read with position $L_i$ ---
Require: $V_m$ {Masking vector for the short read with position $L_i$}
  $E_{SC}(K_P^{Ci}, C_i)$ {Encrypted content with (encrypted) position $E_{OPE}(K_P^O, L_i)$ in $\Delta$}
Ensure: $M\{E_{SC}(K_P^{Ci}, C_i)\}$ {The masked content}
1:   $V_s \leftarrow$ zeros(1, size($V_m$, 2))
2:   for i $\leftarrow$ 1 to size($V_m$, 2) do
3:     if $V_m(i) = 1$ then
4:       $V_s(i) \leftarrow$ Rand {Rand generates a random number from $\{0, 1\}$}
5:     end if
6:   end for
7:   $M\{E_{SC}(K_P^{Ci}, C_i)\} \leftarrow E_{SC}(K_P^{Ci}, C_i) \oplus V_s$

---

Step 11: The biobank conducts the masking by XOR-ing the bits of the encrypted content of each short read (whose position is in $\Delta$), which are set for masking by the MK via the masking vector, with random bits. We describe this process in Algorithm 2. Furthermore, in FIG. 5(a), we illustrate how the masked encrypted content for the corresponding short read is constructed by XOR-ing the random masking string (which is constructed according to the masking vector) with the encrypted content.

Step 12: Finally, the biobank sends the encrypted positions, CSs and decryption keys (generated in Step 10 by the MK) along with the masked contents (generated in Step 11 by the biobank) to the MU. The MU decrypts the received data and obtains the requested nucleotides of the patient.

8 EVALUATION

Focusing on the leakage of genomic data, we evaluate the proposed privacy-preserving system by using real genomic data to show (i) how the leakage of genomic data from the short reads threatens the genomic privacy of a patient, and (ii) how the proposed masking technique helps to prevent this leakage.

Figure 3:
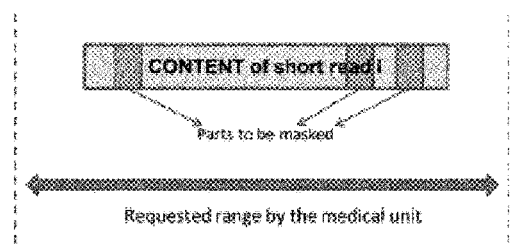

We assume that the MU requests a specific range of nucleotides of patient P (e.g., for a genetic test) from the biobank. As we discussed before, the biobank provides the MU with all the short reads of the patient, which include at least one nucleotide from the requested range. However, as illustrated in FIG. 3, some provided short reads can include out-of-range nucleotides (for which the MU is not authorized), consequently causing leakage of the patient's genomic data (unless there is the proposed masking technique in place).

Figure 4:
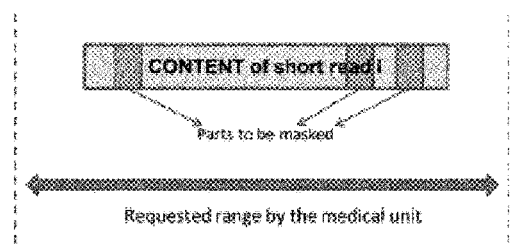
Figure 8:
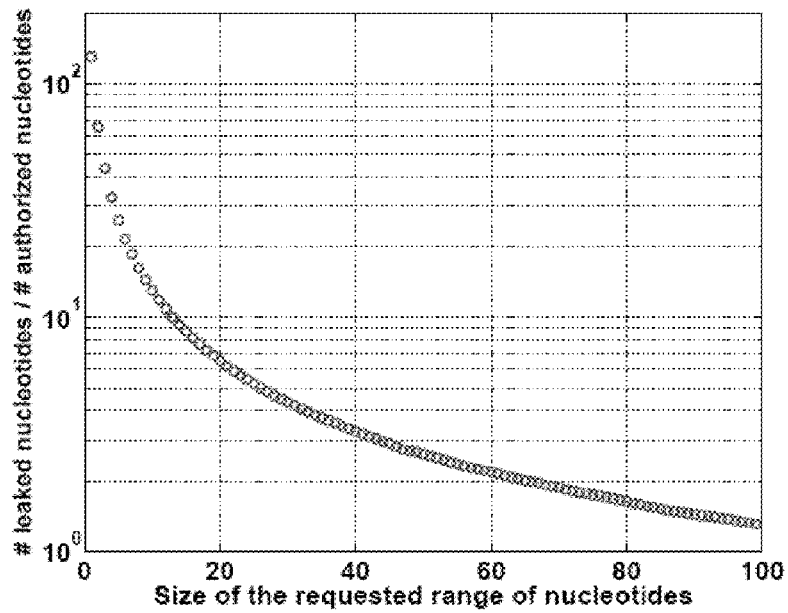
FIG. 8 illustrates the ratio of unauthorized (leaked) genomic data to the authorized data vs. the size of the requested range of nucleotides, when there is no masking in place.

First, without the masking in place, we observe the ratio of unauthorized genomic data (i.e., number of nucleotides provided to the MU that are out of the requested range) to the authorized data (i.e., number of nucleotides within the requested range) for various request sizes. For simplicity, we assume that all the nucleotides within the requested range are considered as authorized and consented data (i.e., the situation in FIG. 4 is not considered; and only those that are out of the requested range (but still provided to the MU via the short reads) are considered as the unauthorized data. For the patient's DNA profile (i.e., SAM file), we use a real human DNA profile (with an average coverage of 10, meaning each nucleotide is present, on the average, in 10 short reads in the SAM file) and we randomly choose the ranges of requested nucleotides from the entire genome of the patient. We illustrate our results in FIG. 8. We observe that for small request sizes, the amount of leakage (of unauthorized data) is very high compared to the size of authorized data. As the leakage vanishes (e.g., the ratio in FIG. 8 becomes 0) with the proposed masking technique, we do not show the leakage when the proposed masking technique is in place in FIGS. 8-11.

Figure 9:
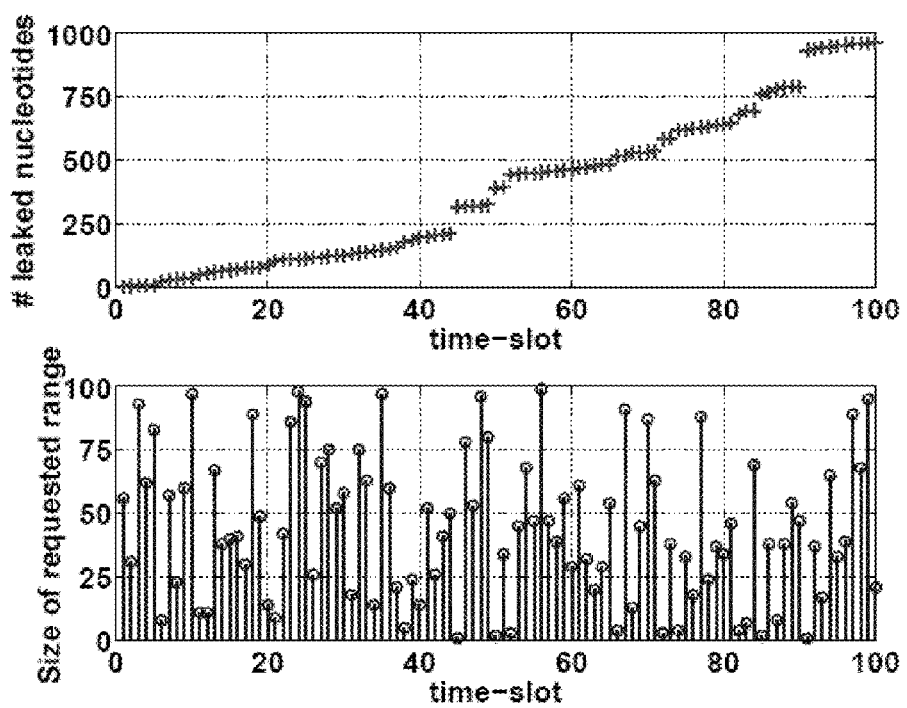
FIG. 9 illustrates the number of leaked nucleotides vs. time for various request sizes, when there is no masking in place.

Using the same DNA profile, we also observe the evolution in the amount of leaked genomic data overtime. For simplicity of the presentation, we assume slotted time and that the MU conducts a genetic test on the patient at each time slot (by requesting a particular range of nucleotides from a random part of his genome). In FIG. 9, we illustrate the amount of genomic data (i.e., number of nucleotides) that is leaked to the MU in 100 time-slots. The jumps in the number of leaked nucleotides (at some time-slots) is due to the fact that some requests might retrieve more short reads comprised of more out-of-range nucleotides. As before, leakage becomes 0 when masking is in place, which shows the crucial role of the proposed scheme.

As discussed in Section 3.2, single nucleotide polymorphisms (SNPs) can reveal a patient's susceptibility to privacy-sensitive diseases. Consequently, leakage of the nucleotides at the SNP positions poses more risk for the genomic privacy of the patient. Therefore, we also study the information leakage, focusing on the leaked SNPs of the patient as a result of different sizes of requests (from random parts of the patient's genome). A number of SNPs is leaked to the MU in 100 time-slots. We observe that the number of leaked SNPs is more than twice the number of authorized SNPs (which are within the requested range of nucleotides). We also observe that the leaked SNPs help to infer privacy-sensitive data about the patient, for instance, his susceptibility to "coronary artery disease" (we further discuss the nature of the leaked SNPs next). When the proposed masking technique is in place, the number of leaked SNPs (outside the requested range) becomes 0.

Finally, we study the genomic data leakage (number of leaked nucleotides and SNPs) when the MU tests the susceptibility of the patient to a particular disease (i.e., when the MU asks for the set of SNPs of the patient that are used to test the corresponding disease). For this study, we use real disease markers.

We note that for this type of test, the size of the requested range of nucleotides (by the MU) for a single SNP is typically 1, but the SNPs are from several parts of the patient's genome. The genomic data leakage of the patient as a result of various disease susceptibility tests each requires a different number of SNPs from different parts of the patient's genome (on the x-axis we illustrate the number of SNPs required for each test). We again observe that the leaked SNPs, as a result of different disease susceptibility tests, reveal privacy-sensitive data about the patient. For example, leaked SNPs of the patient as a result of a test for the Alzheimer's disease could leak information about the patient's susceptibility to "smoking behavior" or "cholesterol" (in Appendix B, we list the nature of some important leaked SNPs due to each susceptibility test) Similar to the previous cases, the number of leaked nucleotides and SNPs is 0 when masking is in place.

9 CRYPTOGRAPHIC TOOLS

Order Preserving Encryption (OPE)

Order-preserving symmetric encryption (OPE) is a deterministic encryption scheme whose encryption function preserves numerical ordering of the plaintexts. OPE was initially proposed by Agrawal et al. (R. Agrawal, J. Kiernan, R. Srikant, and Y. Xu, "Order preserving encryption for numeric data," Proceedings of the 2004 ACM SIGMOD International Conference on Management of Data, pp. 563-574, 2004) and recently re-visited by Boldyreva et al. (A. Boldyreva, N. Chenette, Y. Lee, and A. O'Neill, "Order-preserving symmetric encryption," Proceedings of the 28$^{th}$ Annual International Conference on Advances in Cryptology: the Theory and Applications of Cryptographic Techniques, 2009). Following this document, we briefly introduce OPE next.

For $A, B \subseteq \mathbb{N}$ with $|A| \leq |B|$, a function $f: A \rightarrow 8$ is order-preserving if for all $i, j \in A$, $f(i) > f(j)$ if $i > j$.

We say that a deterministic encryption scheme with plaintext and ciphertext-spaces D, R is order-preserving if $E_{OPE}(K, \cdot)$ is an order-preserving function from D to R for all $K \in K$ (where K is the key space).

Later Boldyreva et al. (A. Boldyreva, N. Chenette, and A. O'Neill, "Order-preserving encryption revisited: Improved security analysis and alternative solutions," Proceedings of the 31st Annual Conference on Advances in Cryptology, pp. 578-595, 2011) conducted a security analysis of OPE. We note that (as acknowledged by the authors) some security bounds established in this publication are not useful when the adversary has access to a large number of cipher texts in the database (as in our work, in which a curious party at the biobank can access hundreds of millions of cipher texts per patient). However, this does not mean that the security of OPE is low for these scenarios; it only means that the formal bounds in Boldyreva are not helpful to determine the level of security for these cases.

Stream Cipher (SC)

A stream cipher is a symmetric key cipher, where plaintext digits are combined with a pseudorandom cipher digit stream (key stream). In a stream cipher each plaintext digit is encrypted one at a time with the corresponding digit of the key stream, to give a digit of the ciphertext stream. In general, a digit is typically a bit and the encryption operation is an XOR. For example, the message m is encrypted as H(key, nonce)⊕ m, where H is a pseudorandom function.

The invention claimed is:

1. Method to request by a medical unit (MU) a range of nucleotides of genomic data in a privacy preserving manner stored in a biobank, the genomic data comprising a plurality of short reads aligned to a reference deoxyribonucleic acid (DNA) sequence, the biobank storing, for each short read:
encrypted nucleotides,
an encrypted cigar string, and
an encrypted position in the reference DNA sequence, the encrypted position being encrypted with an order preserving encryption algorithm,
wherein the range comprises a lower bound and an upper bound, and
wherein the method comprises:
encrypting, by the medical unit, the lower and upper bound with the order preserving encryption algorithm,
sending, by the medical unit, the encrypted lower bound and upper bounds to the biobank,
retrieving, by the biobank, all short reads which include at least one nucleotide for the requested range of nucleotides,
masking, by the biobank, nucleotides of the retrieved short reads outside the range defined by the encrypted lower and upper bounds, and
providing the masked retrieved short reads to the medical unit (MU).

2. The method of claim 1, wherein retrieving all short reads which include at least one nucleotide for the requested range of nucleotides further comprise:
sending, by the biobank, the encrypted lower and upper bounds to a masking and key manager MK;
decrypting, with the masking and key manager MK, the encrypted lower bound;
adjusting the lower bound as the decrypted lower bound minus the maximum length of a short read;
encrypting, with the order-preserving encryption algorithm, adjusted nucleotide position range defined by the adjusted lower bound; and
sending the encrypted adjusted lower bound and encrypted upper bound range to the biobank.

3. The method according to claim 1, wherein masking further comprises:
sending, by the biobank to a masking and key manager MK, all retrieved short reads which include at least one nucleotide for the requested range of nucleotides; and
marking, by the masking and key manager MK, with a masking vector, parts of the requested short reads with nucleotides which are out of the requested range of nucleotides.

4. The method according to claim 2, wherein masking further comprises:
sending, by the biobank to a masking and key manager MK, all retrieved short reads which include at least one nucleotide for the requested range of nucleotides; and
marking, by the masking and key manager MK, with a masking vector, parts of the requested short reads with nucleotides which are out of the requested range of nucleotides.

5. The method according to claim 1, wherein the encrypted nucleotides are encrypted with a stream cipher algorithm.

6. The method according to claim 5, further comprising XOR-ing the encrypted nucleotides with a random masking string for a corresponding masking vector.

7. The method according to claim 2, wherein the encrypted nucleotides are encrypted with a stream cipher algorithm.

8. The method according to claim 7, further comprising XOR-ing the encrypted nucleotides with a random masking string for a corresponding masking vector.

9. The method according to claim 3, wherein the encrypted nucleotides are encrypted with a stream cipher algorithm.

10. The method according to claim 9, further comprising XOR-ing the encrypted nucleotides with a random masking string for a corresponding masking vector.

11. The method according to claim 4, wherein the encrypted nucleotides are encrypted with a stream cipher algorithm.

12. The method according to claim 11, further comprising XOR-ing the encrypted nucleotides with a random masking string for a corresponding masking vector.

13. The method according to claim 1, further comprising modifying a cigar string of the requested short reads with nucleotides marked for masking such that the marked nucleotides for masking are represented with a new operation code in the cigar string.

14. The method according to claim 2, further comprising modifying a cigar string of the requested short reads with nucleotides marked for masking such that the marked nucleotides for masking are represented with a new operation code in the cigar string.

15. The method according to claim 3, further comprising modifying a cigar string of the requested short reads with nucleotides marked for masking such that the marked nucleotides for masking are represented with a new operation code in the cigar string.

16. The method according to claim 4, further comprising modifying a cigar string of the requested short reads with nucleotides marked for masking such that the marked nucleotides for masking are represented with a new operation code in the cigar string.

17. The method according to claim 5, further comprising modifying a cigar string of the requested short reads with nucleotides marked for masking such that the marked nucleotides for masking are represented with a new operation code in the cigar string.

18. The method according to claim 6, further comprising modifying a cigar string of the requested short reads with nucleotides marked for masking such that the marked nucleotides for masking are represented with a new operation code in the cigar string.

19. The method of claim 1, wherein the encrypted cigar string, for each short read, is encrypted with a symmetric encryption algorithm.

20. The method of claim 1, wherein the encrypted nucleotides are encrypted with a stream cipher algorithm.

* * * * *